US008731954B2

(12) United States Patent
Heinze et al.

(10) Patent No.: US 8,731,954 B2
(45) Date of Patent: May 20, 2014

(54) AUDITING THE CODING AND ABSTRACTING OF DOCUMENTS

(75) Inventors: Daniel T. Heinze, San Diego, CA (US); Peter Feller, La Mesa, CA (US); Mark L. Morsch, San Diego, CA (US)

(73) Assignee: A-Life Medical, LLC, San Diego, CA (US)

( * ) Notice: Subject to any disclaimer, the term of this patent is extended or adjusted under 35 U.S.C. 154(b) by 973 days.

(21) Appl. No.: 11/692,093

(22) Filed: Mar. 27, 2007

(65) Prior Publication Data

US 2007/0226211 A1  Sep. 27, 2007

Related U.S. Application Data

(60) Provisional application No. 60/786,507, filed on Mar. 27, 2006.

(51) Int. Cl.
*G06Q 50/00* (2012.01)
*G06Q 50/22* (2012.01)

(52) U.S. Cl.
CPC ....................................... *G06Q 50/22* (2013.01)
USPC ............................................................ 705/2

(58) Field of Classification Search
CPC .................... G06Q 50/22–50/24; G06Q 40/08
USPC ........................................................ 705/2–3
See application file for complete search history.

(56) References Cited

U.S. PATENT DOCUMENTS

| | | |
|---|---|---|
| 3,996,672 A | 12/1976 | Osofsky et al. |
| 5,307,262 A * | 4/1994 | Ertel .................................. 705/2 |
| 5,325,293 A | 6/1994 | Dorne |
| 5,483,443 A | 1/1996 | Milstein et al. |
| 5,583,758 A | 12/1996 | McIlroy et al. |
| 5,594,638 A | 1/1997 | Iliff |
| 5,619,709 A | 4/1997 | Caid et al. |
| 5,675,819 A | 10/1997 | Schuetze |
| 5,680,511 A | 10/1997 | Baker et al. |
| 5,778,157 A | 7/1998 | Oatman et al. |
| 5,794,178 A | 8/1998 | Caid et al. |
| 5,809,476 A | 9/1998 | Ryan |
| 5,873,056 A | 2/1999 | Liddy et al. |
| 5,900,871 A | 5/1999 | Atkin et al. |
| 5,995,955 A | 11/1999 | Oatman et al. |
| 6,055,494 A | 4/2000 | Friedman |
| 6,081,774 A | 6/2000 | De Hita et al. |

(Continued)

OTHER PUBLICATIONS

Neubauer, Aljoscha Steffen. "The EWMA control chart", Clinical Chemistry, 43:4, pp. 594-601, 1997.*

(Continued)

*Primary Examiner* — Robert Morgan
*Assistant Examiner* — Robert Sorey
(74) *Attorney, Agent, or Firm* — Dorsey & Whitney LLP

(57) ABSTRACT

Techniques for implementing Quality Assurance of the process of coding medical documents are disclosed. An audit of a coding process for a medical document is initiated by selecting and setting audit parameters. Using the selected parameters, a sample batch of coded documents is obtained from a universe of coded documents. The sample batch of coded documents is presented to auditor(s), and the auditor(s) provide corrections, which are recorded, and a score for each correction is calculated. A sample score, based on the corrections, is calculated in a manner that tracks to subjective auditor assessments of the process quality as being acceptable, marginally acceptable, or unacceptable, and which sample score accounts for the individual auditor subjectivity and an error.

30 Claims, 15 Drawing Sheets

(56) References Cited

U.S. PATENT DOCUMENTS

| | | | |
|---|---|---|---|
| 6,137,911 A | 10/2000 | Zhilyaev | |
| 6,182,029 B1 | 1/2001 | Friedman | |
| 6,389,405 B1 | 5/2002 | Oatman et al. | |
| 6,498,982 B2 | 12/2002 | Bellesfield et al. | |
| 6,529,876 B1* | 3/2003 | Dart et al. | 705/4 |
| H2098 H | 3/2004 | Morin | |
| 6,866,510 B2 | 3/2005 | Polanyi et al. | |
| 6,915,254 B1 | 7/2005 | Heinze et al. | |
| 7,043,426 B2 | 5/2006 | Roberge et al. | |
| 7,174,507 B2 | 2/2007 | Baudin et al. | |
| 7,359,861 B2 | 4/2008 | Lee | |
| 7,360,151 B1 | 4/2008 | Froloff | |
| 7,369,998 B2 | 5/2008 | Sarich et al. | |
| 7,493,326 B2* | 2/2009 | Bishop et al. | 707/781 |
| 7,624,027 B1 | 11/2009 | Stern et al. | |
| 7,653,641 B2* | 1/2010 | Theissen et al. | 1/1 |
| 7,908,552 B2 | 3/2011 | Heinze | |
| 7,949,538 B2 | 5/2011 | Heinze | |
| 2002/0010714 A1 | 1/2002 | Hetherington | |
| 2002/0156810 A1 | 10/2002 | Holland et al. | |
| 2003/0018251 A1 | 1/2003 | Solomon | |
| 2003/0033347 A1 | 2/2003 | Bolle et al. | |
| 2003/0115195 A1* | 6/2003 | Fogel et al. | 707/3 |
| 2004/0093293 A1* | 5/2004 | Cheung | 705/36 |
| 2004/0117734 A1 | 6/2004 | Krickhahn | |
| 2004/0172297 A1* | 9/2004 | Rao et al. | 705/2 |
| 2004/0254816 A1 | 12/2004 | Myers | |
| 2005/0071185 A1* | 3/2005 | Thompson | 705/1 |
| 2005/0091067 A1* | 4/2005 | Johnson | 705/1 |
| 2005/0261910 A1 | 11/2005 | Precoda et al. | |
| 2005/0273361 A1* | 12/2005 | Busch | 705/2 |
| 2006/0059021 A1* | 3/2006 | Yulman et al. | 705/4 |
| 2006/0129922 A1 | 6/2006 | Walker | |
| 2006/0134750 A1* | 6/2006 | Liu et al. | 435/69.1 |
| 2006/0247949 A1* | 11/2006 | Shorrosh | 705/2 |
| 2007/0061348 A1 | 3/2007 | Holland et al. | |
| 2007/0094030 A1 | 4/2007 | Xu | |
| 2007/0226211 A1 | 9/2007 | Heinze et al. | |
| 2008/0222518 A1 | 9/2008 | Walker | |
| 2008/0256108 A1 | 10/2008 | Heinze et al. | |
| 2008/0256329 A1 | 10/2008 | Heinze et al. | |
| 2008/0282153 A1 | 11/2008 | Kindeberg et al. | |
| 2009/0070140 A1 | 3/2009 | Morsch et al. | |
| 2009/0144617 A1 | 6/2009 | Funes et al. | |
| 2009/0175550 A1 | 7/2009 | Taleb | |
| 2010/0064131 A1 | 3/2010 | Spatscheck et al. | |
| 2010/0195909 A1 | 8/2010 | Wasson et al. | |
| 2010/0257444 A1 | 10/2010 | Bever et al. | |

OTHER PUBLICATIONS

Department of Health and Human Services—OIG Office of Audit Services. Rat-Stats Companion Manual, Sep. 2001.*
Department of Health and Human Services—OIG Office of Audit Services. Rat-Stats User Guide, Sep. 2001.*
Gregory, Tom. "Interpreting Error Rates in Health Care Billing Audits," Journal of Health Care Compliance; Jan./Feb. 2003; 5, 1; p. 4.*
Friedman, et al. "Natural language processing in an operational clinical information system," Natural Language Engineering, vol. 1(1): 83-108 (May 1995).
Zingmond and Lenert. "Monitoring Free-Text Data Using Medical Language Processing," Computers and Biomedical Research, vol. 26: 467-481 (1993).
Lehnert, Soderland, Aronow, Feng, and Shmueli. "Inductive Text Classification for Medical Applications," to appear in Journal for Experimental and Theoretical Artificial Intelligence, Brookline, MA (date unknown).
Larkey and Croft. "Automatic Assignment of ICD9 Codes to Discharge Summaries," UMass Center for Intelligent Information Retrieval, Amherst, MA (date unknown).
Sneiderman, Rindflesch, and Aronson. "Finding the Findings: Identification of Findings in Medical Literature Using Restricted Natural Language Processing," Bethesa, MD (1996).
Aronow, Cooley, and Soderland. "Automated Identification of Episodes of Asthma Exacerbation for Quality Measurement in a Computer-Based Medical Record," Brookline, MA and Amherst, MA (date unknown).
Croft, Callan, and Aronow. "Effective Access to Distributed Heterogeneous Medical Text Databases," MEDINFO 96 Proceedings, Amherst, MA (1995).
Aronow, Soderland, Feng, Croft and Lehnert. "Automated Classification of Encounter Notes in a Computer Based Medical Record," Amherst, MA (date unknown).
Aronow and Shmueli. "A PC Classifier of Clinical Text Documents: Advanced Information Retrieval Technology Transfer," Amherst, MA (1996).
Aronow and Feng, "Ad-Hoc Classification of Electronic Clinical Documents," D-Lib Magazine, Amherst, MA, 1997.
Soderland, Aronow, Fisher, Aseltine and Lehnert. "Machine Learning of Text Analysis Rules for Clinical Records," Amherst, MA and Brookline, MA (date unknown).
Yang and Chute. "An Application of Least Squares Fit Mapping to Clinical Classification," 16.sup.th Annual Symposium on Computer Application in Medical Care, pp. 460-464, Rochester, MN (1993).
Ranum. "Knowledge Base Understanding of Radiology Text," 12.sup.th Annual Symposium on Computer Application in Medical Care, pp. 141-145, Rochester, MN (1988).
Sager, Lyman, Nhan, and Trick. "Automatic Encoding into SNOMED III: A Preliminary Investigation," 18.sup.th Annual Symposium on Computer Application in Medical Care, pp. 230-234, New York, NY (1994).
Lenert and Tovar. "Automated Linkage of Free-Text Descriptions of Patients with a Practice Guideline," 17.sup.th Annual Symposium on Computer Application in Medical Care, pp. 274-278, Stanford, CA (1993).
Sager, Lyman, Bucknail, Nhan, and Trick. "Natural Language Processing and the Representation of Clinical Data," Journal of the American Medical Information Association, vol. 1, No. 2, pp. 142-160, New York, NY (Mar./Apr. 1994).
Furuse et al. "Constituent Boundary Parsing for Example-Based Machine Translation," Google, pp. 105-111 (1994).
Starosta et al. "Lexicase Parsing: A Lexicon-driven Approach to Syntactic Analysis," Google, pp. 127-132 (1986).
"Introducing SNOMED CT" (online) [Retrieved Dec. 21, 2010]; Retrieved from the Internet URL: www.ihtsdo.org/publications/introducing-snomed-ct/; 2 pgs.
"Value Proposition for SNOMED CT" (online) [Retrieved Dec. 21, 2010]; Retrieved from the Internet URL: www.ihtsdo.org/fileadmin/user$_{13}$ upload/Docs_01/Publications/SNOMED_CT/SNOMED_CT_Benefits_v4.pdf; 3 pgs.
"SNOMED Clinical Terms User Guide Jan. 2010 International Release (US English)" (online) [Retrieved Dec. 21, 2010]; Retrieved from the Internet URL: www.ihtsdo.org/fileadmin/user_upload/Docs_01/Publications/doc_userguide_current-en-US_INT_20100131.pdf.; 99 pages.
"SNOMED Clinical Terms Overview" (online) [Retrieved Dec. 21, 2010]; retrieved from the Internet URL: www.ihtsdo.org/fileadmin/user_upload/Docs_01/Recourses/Introducing_SNOMED_CT/SNOMED_CT_Overview)_IHTSDO_Taping_Aug08.pdf.; 82 pgs.
"SNOMED Clinical Terms Basics" (online) [Retrieved Dec. 21, 2010]; retrieved from the Internet URL: www.ihtsdo.org/fileadmin/user_upload/Docs_01/Recourses/Introducing_SNOMED_CT/SNOMED_CT_Basics_IHTSDO_Taping_Aug08.pdf.; 82 pgs.
"SNOMED Clinical Terms Fundamentals" (online) [Retrieved Dec. 21, 2010]; retrieved from the Internet URL: www.ihtsdo.org/fileadmin/user_upload/docs_01/SNOMED_Clinical_Terms_Fundamentals.pdf.; 56 pgs.
"SNOMED CT Browsers" (online) [Retrieved Dec. 21, 2010]; Retrieved from the Internet URL: www.nim.nih.gov/research/umls/Snomed/snomed_browsers.html; 2 pgs.
"HL7 Clinical Document Architecture, Release 2.0" (online) [Retrieved Dec. 20, 2010]; Retrieved from the Internet URL: www.hl7.org/v3ballot/html/foundationdocuments/cda/cda.htm; 190 pgs.

* cited by examiner

FIG. 5H

AUDITING THE CODING AND ABSTRACTING OF DOCUMENTS

CLAIM OF PRIORITY

This application claims priority under 35 USC §119(e) to U.S. Patent Application Ser. No. 60/786,507, filed on Mar. 27, 2006, the entire contents of which are hereby incorporated by reference.

TECHNICAL FIELD

The following disclosure relates to techniques for scoring or otherwise evaluating coded medical documents (where "coding" refers to the process of identifying document contents, including medical findings, diagnoses and procedures, using a set of alpha-numeric medical codes) to assess a quality of a process used to code the documents. In particular, the disclosure relates to methods and computerized tools for auditing and performing Quality Assurance (QA) tasks on processes (both automated and manual) of coding and abstracting documents.

BACKGROUND

In general, a process for coding documents (e.g., medical documents) can be performed manually by a human coder or at least semi-automatically using a machine (e.g., a computer system). Quality assurance of a coding process tend to be performed by a human auditor.

SUMMARY

Techniques for implementing a system for auditing a coding process are disclosed.

In one aspect, coded documents are evaluated by receiving one or more audit parameters. A sample batch of coded documents from a universe of coded documents is selected based at least in part on the received audit parameters. One or more documents of the selected sample batch is processed to calculate a document score for each processed document based on corrections corresponding to the processed document received from one or more auditors. In addition, a sample score is calculated based on a function of the document scores. The sample score correlates to subjective auditor assessments of a coding process used to code the selected sample batch of coded documents.

In another aspect, a system for evaluating coded documents includes a user interface device and one or more computers communicatively coupled to the user interface device. The one or more computers include a processor and a display designed to provide a graphical user interface to multiple auditors. The graphical user interface is designed to receive from the auditors one or more audit parameters. The graphical user interface is also designed to allow the auditors to select a sample batch of coded documents from a universe of coded documents based on the received audit parameters. The graphical user interface is used to present the selected sample batch of coded documents to the auditors. Corrections from the auditors can also be received using the graphical user interface The graphical user interface is also be used to facilitate calculation of a document score for each processed document. The graphical user interface also facilitates calculation of a sample score based on a function of the document scores. The sample score correlates to subjective auditor assessments of a coding process used to code the selected sample batch of coded documents.

Implementations can optionally include one or more of the following features. The received corrections can be recorded. The sample score can be calculated based on a function including a summation of the calculated document scores. The sample score can optionally be calculated by defining a quality of the coding process as being one of an acceptable quality, a marginal quality and an unacceptable quality. In addition, a weight can be assigned to each of various factors used in calculating the document score. The document score can be calculated based on the received corrections by aggregating the weights assigned to the factors. Also, a defect level can be calculated based on the sample score. Further, the defect level can be adjusted to account for subjectivity and error of the auditors.

Implementations can further optionally include one or more of the following features. The received audit parameters can be controlled to change a size of the sample batch. Also, a level of auditor subjectivity and error can be empirically established. In addition, an upper control limit and a lower control limit can be established based on the empirically established level of auditor subjectivity and error. The sample score can be compared against the upper and lower control limits to determine whether the coding process is in control. The audit can be repeated over a period of time to compile multiple sample scores and track a measure of variance in the sample scores across the period of time. Further, a measure of variance among the different auditors can be tracked.

The subject matter described in this specification can be implemented as a method or as a system or using computer program products, tangibly embodied in information carriers, such as a CD-ROM, a DVD-ROM, a semiconductor memory, and a hard disk. Such computer program products may cause a data processing apparatus to conduct one or more operations described in this specification.

In addition, the subject matter described in this specification can also be implemented as a system including a processor and a memory coupled to the processor. The memory may encode one or more programs that cause the processor to perform one or more of the method acts described in this specification.

Further, these aspects can be implemented using an apparatus, a method, a system, a computer program product or any combination of an apparatus, a method, a system and a computer program product. The details of one or more embodiments are set forth in the accompanying drawings and the description below. Other features, objects, and advantages will be apparent from the description and drawings, and from the claims.

DESCRIPTION OF DRAWINGS

FIGS. 5A, 5B, 5C, 5D, 5E, 5F, 5G, 5H, 5I, 5J and 5K are various screenshots of a graphical user interface (GUI) for facilitating auditing of a coding process.

Like reference symbols in the various drawings indicate like elements.

DETAILED DESCRIPTION

Techniques are disclosed for implementing Quality Assurance of a process of coding medical documents. The techniques can be implemented to apply to other audit tasks such as complex evaluation of each product item (e.g., coded document) and accounting for a level of subjectivity and error of a human auditor in judging the correctness of the coding process.

Medical coding and abstracting ("coding") is a process of mapping the clinical content of clinical documents to standardized nomenclatures and ontologies in which individual clinical concepts are signified by alphanumerical respective nomenclature codes. Each of the nomenclature codes in ontology, optionally stands in some relation to one or more of the remaining codes. Traditionally, coding has been done "manually" by humans. Because the volume of medical documents being manually coded at any one location has, in the past, been relatively small, Quality Assurance (QA) of the coding process has primarily depended on the individual skills, training and continuing education of the coders. In the field of medical coding, QA methods historically consist of an ad hoc review of some fixed number or percentage of a human coder's work product with ad hoc or subjective scoring and evaluation of the coder's audit results. Audit results across a time period and between locations (e.g., different auditors) tend not to be comparable (i.e., a large variation). Such varied results may provide minimal protection in case of an investigation by federal or private insurance payers. The recent advent of automated systems that use Natural Language Processing (NLP) techniques to code millions of reports a month through a single computerized site has only increased the burden on human QA auditors.

An automated system for coding can be implemented based on a LifeCode® NLP system (available from A-Life Medical of San Diego, Calif.) for coding and abstracting clinical documents. The LifeCode® NLP system is described in detail in U.S. Pat. No. 6,915,254, which is incorporated by reference in its entirety. Coding is a complex process, and for any given medical document there may be a diversity of opinions on the correct coding process. Further, due to the complexity of the coding process, even skilled auditors are expected to make some errors in judgment. Therefore, both matters of opinion (subjective judgment) and factual errors may be considered when conducting a medical coding audit.

Audit System

Figure 1A:
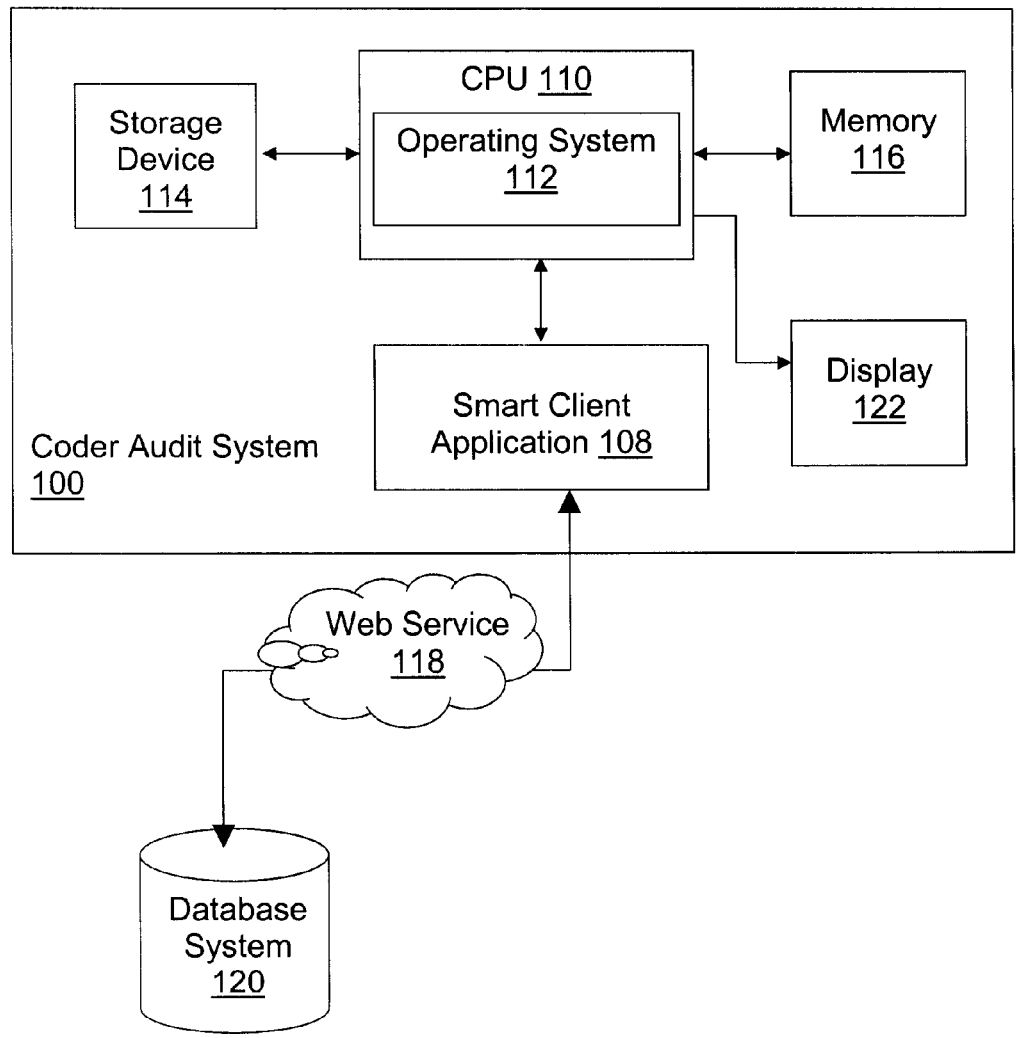
FIG. 1A is a functional block diagram of a coder audit system.

FIG. 1A is a functional diagram of a coder audit system 100 for implementing Quality Assurance of a process of coding medical documents. The coder audit system 100 can be implemented to execute a smart client application 108, which accesses a database server 120 through a communication link 118. The smart client application 108 can be implemented using VirtualBasic.NET (VB.NET) or other suitable programming language. The coder audit system 108 executing the smart client application 108 can be a computer system such as a local server in communication with one or more internal and/or external servers through the communication link 118. The communication link 118 can include a wired or wireless network communication protocol. A wired network communication protocol can include local areas network (LAN), wide area network (WAN), broadband network connection such as Cable Modem, Digital Subscriber Line (DSL). A wireless network communication protocol can include WiFi, WIMAX and BlueTooth.

The coder audit system 100 implemented as a computer system can includes one or more computers. Each computer in the computer system includes a central processing unit (CPU) 110 executing a suitable operating system 112, a storage device 114, a memory device 116, and a display device 122. The storage device can include nonvolatile memory units such as a read only memory (ROM), a CD-ROM, a programmable ROM (PROM), erasable program ROM (EPROM), and a hard drive. The memory device can include volatile memory units such as random access memory (RAM), dynamic random access memory (DRAM), synchronous DRAM (SDRAM), double DRAM (DDRAM), etc. A display device 122 can include a Cathode-Ray Tube (CRT) monitor, a liquid-crystal display (LCD) monitor, or other suitable display devices. Other suitable computer components such as input/output devices can be included in the coder audit system 108.

In some implementations, the coder audit system 100 is implemented entirely as a web application such as the smart client application 108. The coder audit system 100 can be implemented as other suitable web/network-based applications using other suitable web/network-based computer languages. For example, an Active Server Page (ASP), and a JAVA Applet can be implemented. In some implementations, the coder audit system 100 is implemented using local computer applications executing in a local computer system for accessing one or more databases stored in a local storage device such as the storage device 114 or other suitable local storage devices (not shown).

Universe Selection Parameters

Figure 1B:
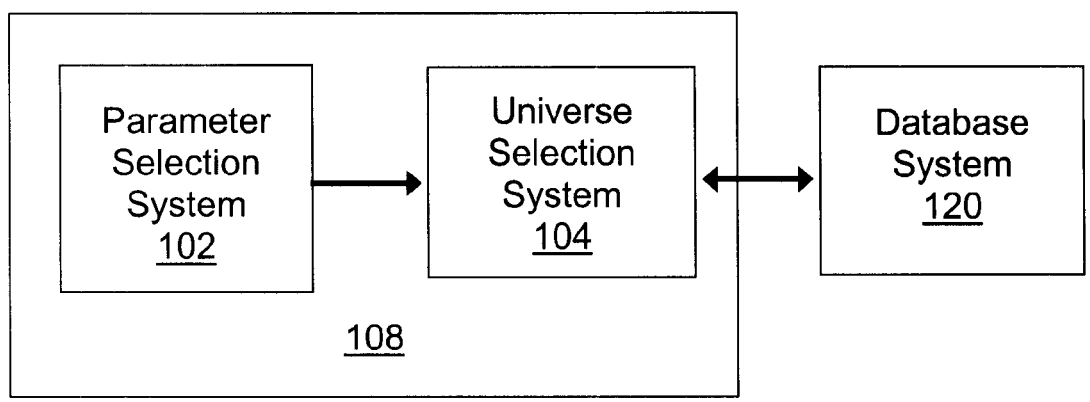
FIG. 1B is a detailed view of a smart client application.

FIG. 1B is a detailed view of the smart client application 108 executing on the coder audit system 100. The smart client application 108 includes a parameter selection system 102 and a universe selection system 104. The parameter selection system 102 functions to receive and set the parameters used to select the universe of documents (individual products) from which a sample audit batch can be selected. In medical applications, the selected parameters can include (but are not limited to) date(s) of medical service rendered, location(s) of medical service rendered, physician(s), particular codes used, type(s) of codes used, particular ontological relations between codes, payer (e.g., insurance payer), payer class, document status (e.g. pending, billed, paid, etc.), and coder(s) (i.e. what person(s) or automated coding system produced the codes). The universe selection system 104 takes the parameters set by the parameter selection system 102 and automatically selects a universe (e.g., one or more databases) from which a sample audit batch of documents can be selected. For example, a universe can selected from one or more computerized database systems 120 storing the work products (documents) to be audited. In some implementations, other suitable local and external storage and selection mechanisms can be implemented as the available universe.

In some implementations, the universe selection system 104 is configured to retrieve the entire universe of individual products that matches the selection parameters. In other implementations, the universe selection system 104 is configured to retrieve only a sample of the universe.

The smart client application 108 allows a user to create new audit batches or open existing ones. Creation of an audit batch is implemented using a wizard style graphical user interface (GUI). Using the GUI, the coder audit system 100 can receive audit parameters used to initiate an audit. The GUI is described further in detail with respect to FIGS. 5A, 5B, 5C, 5D, 5E, 5F, 5G, 5H, 5I, 5J and 5K. The received audit parameters can be saved or recorded for later retrieval when initiating a new audit.

Figure 2:
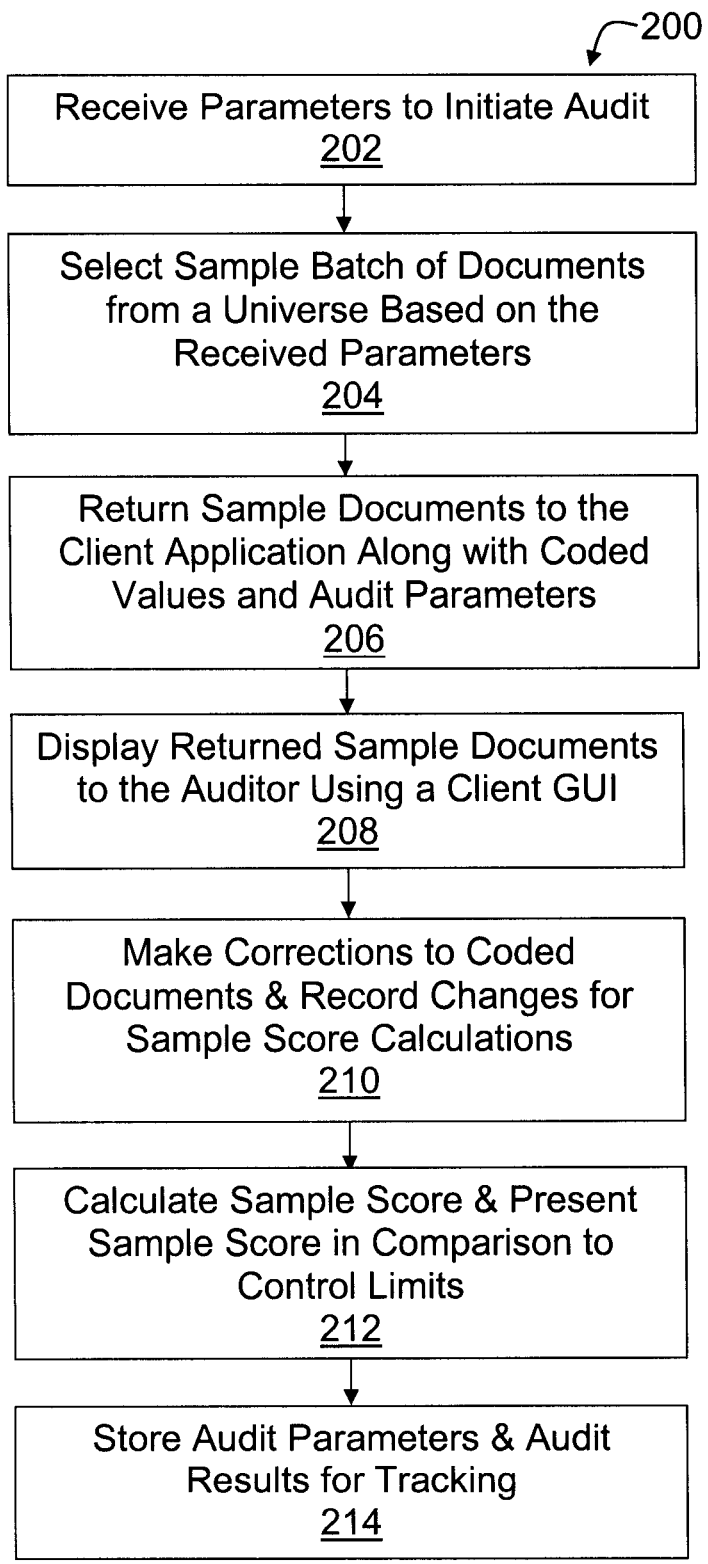
FIG. 2 is a process flow diagram of a process for auditing coding and abstracting of documents.

FIG. 2 describes a process 200 for implementing the coder audit system 100. The process 200 facilitates Quality Assurance of a coding process used to code medical documents under audit. A user (e.g., a human auditor) interfaces with the coder audit system 100 using a GUI and selects one or more parameters for initiating an audit of a sample set of coded medical documents at 202. The system 100 receives the parameters selected. Based on the selected parameters, the smart client application 108 is executed to send a web service request to extract the appropriate documents (e.g., a sample batch of documents) from a universe of documents (e.g., one or more web server databases 120) at 204. A sample batch of documents are returned to the smart client application 108 along with the coded values and any other chosen audit parameters at 206. The sample batch of documents returned to the smart client application 108 with codes are displayed to the auditor on the display device 122 of the coder audit system 100 using a client GUI at 208. The client GUI allows the auditor to make corrections to each coded document and automatically record the corrections and their types for calculating document and sample scores at 210. In addition, multiple documents within the sample audit batch can be viewed and compared together using mechanisms such as the GUI.

At the conclusion of an audit, a document score is calculated for each document and an overall sample score is calculated for the sample batch of documents. The calculated scores are presented in comparison to predefined control limits at 212. The control limits includes an upper control limit and a lower control limit. Audit parameters for each session are stored a storage unit (e.g., the web server database 120) and may be reused and/or modified from one audit session to the next at 214. Audit results are also stored in the web server database 120 for tracking the results across a time period. For example an X-bar chart can be implemented to illustrate comparisons of different coding processes at 214.

Performance Limits

To test the calculated sample scores, two sets of performance limits are defined: (1) specification limits and (2) control limits. The specification limits are related to individual components of the production items under test. The specification limits can be judged as either correct or incorrect (pass/fail). If judged incorrect (fail), the specification limits can optionally be judged as either of consequence or not of consequence. The control limits are statistically defined limits that indicate whether the overall coding process under audit is in control or not in control. When a process under audit, as measured in terms of proportion of errors, rises above the upper control limit, some adverse consequences are indicated. Likewise when a process under audit falls below the lower control limit, some adverse consequences may be indicated. However, for some processes such as coding, when the coding process falls below the lower control limit, no adverse consequence is indicated, since this indicates that the coding process is performing better than required or expected. The process under audit can also be measured in terms of a proportion of correct items, in which case the interpretation of the control limits would be reversed.

In one aspect, standard sample selection and control limit formulas are revised and augmented to account for the level of auditor subjectivity and error present. In addition, guidance is provided regarding the selection of meaningful parameters and interpretation of results when using the revised formulas.

Sample Selection and Control Limits

The coder audit system 100 can be implemented to apply a standard sample selection formula, Equation (1), to define the preferred parameters and formulas for selecting an unrestricted random sample, fpc*n, from a universe of size N.

$$X = x - (CV * P * fpc * n) \quad (1)$$

Equation (1) can be revised and augmented as follows. A raw defect number, x, is recalculated to provide a modified defect number, X, to account for the expected subjectivity and error of the auditor. If the error level of the auditor is CV and the auditee is expected to make proportion P errors, then the number of correct auditee codes incorrectly judged as errors by the auditor is CV*P*fpc*n, which is subtracted from the raw defect number x. In some implementations, other parameters and formulas can be used to select the sample size and adjust the defect number and still account for auditor (tester) error and subjectivity. For example, n can be derived based on the population mean and standard deviation rather than on the population error proportion. Sample selection and control limits can be calculated using the following parameters. Note that the following parameters are expressed as percentages, probabilities or proportions depending primarily on how they are used in common parlance. When working with the definitions and formulae, care should be taken to understand the units and make adjustments as needed.

CV is the expected or observed judgment subjectivity/error proportion of the auditor.
CL is the desired confidence level as a percent.

$$CL <= 100*(1-CV) \text{ is preferred.}$$

Z is the area under the tails of the distribution for the desired CL.
H is the percentage half width of the desired confidence interval where H>=CV (with CV also expressed as a percentage). H>=CV+1 is preferred.
P is the expected auditee proportion of errors.
N is the size of the universe of documents to be sampled.
n is the unadjusted sample size, where $$n = (Z^2 * P * (1-P))/H^2.$$

fpc is the finite population correction factor, where $$fpc = SQRT((N-n)/(N-1)).$$

fpc*n is the adjusted sample size.
x is the observed defect/error number.
X is the defect/error number adjusted for the auditor error rate, where X=x−(CV*P*fpc*n).
e is the sample proportion of defects x/fpc*n.
E is the adjusted sample proportion of defects X/fpc*n.
UCL is the upper control limit, where $$UCL = P + (Z*(SQRT(P*(1-P)/fpc*n))).$$

LCL is the lower control limit, where $$LCL = P - (Z*(SQRT(P*(1-P)/fpc*n))).$$

To facilitate proper usage of the revised formulas in selection of meaningful parameters and interpretation of results, the following specific guidance is provided:

1. CV, the expected or observed auditor subjectivity and error, conforms to CV>=3% (or 0.03 as a probability).
2. The half-width, H, of the desired confidence interval should be greater than CV, the error proportion of the auditor. No matter how large the sample, the confidence level of the audit results cannot be greater than the confidence level for the auditor. Thus, increasing the sample size, which is the practical effect of decreasing H, will not truly improve precision once H<=CV. For example, H>=CV+1% (or 0.01 as a probability).
3. CL>=100*(1−CV) where CL is a percent and CV is a probability, because similar to H, a confidence level in the audit cannot be greater than the maximum accuracy of the auditor.

Specification Limits

Diagnoses and findings are coded using the International Classification of Diseases, 9$^{th}$ Clinical Modification (ICD-9-CM) [available from US Dept. of Health and Human Services] and procedures and level of service are coded using the Current Procedural Terminology (CPT) [available form American Medical Association]. In some implementations other suitable coding systems may be substituted.

Figure 3:
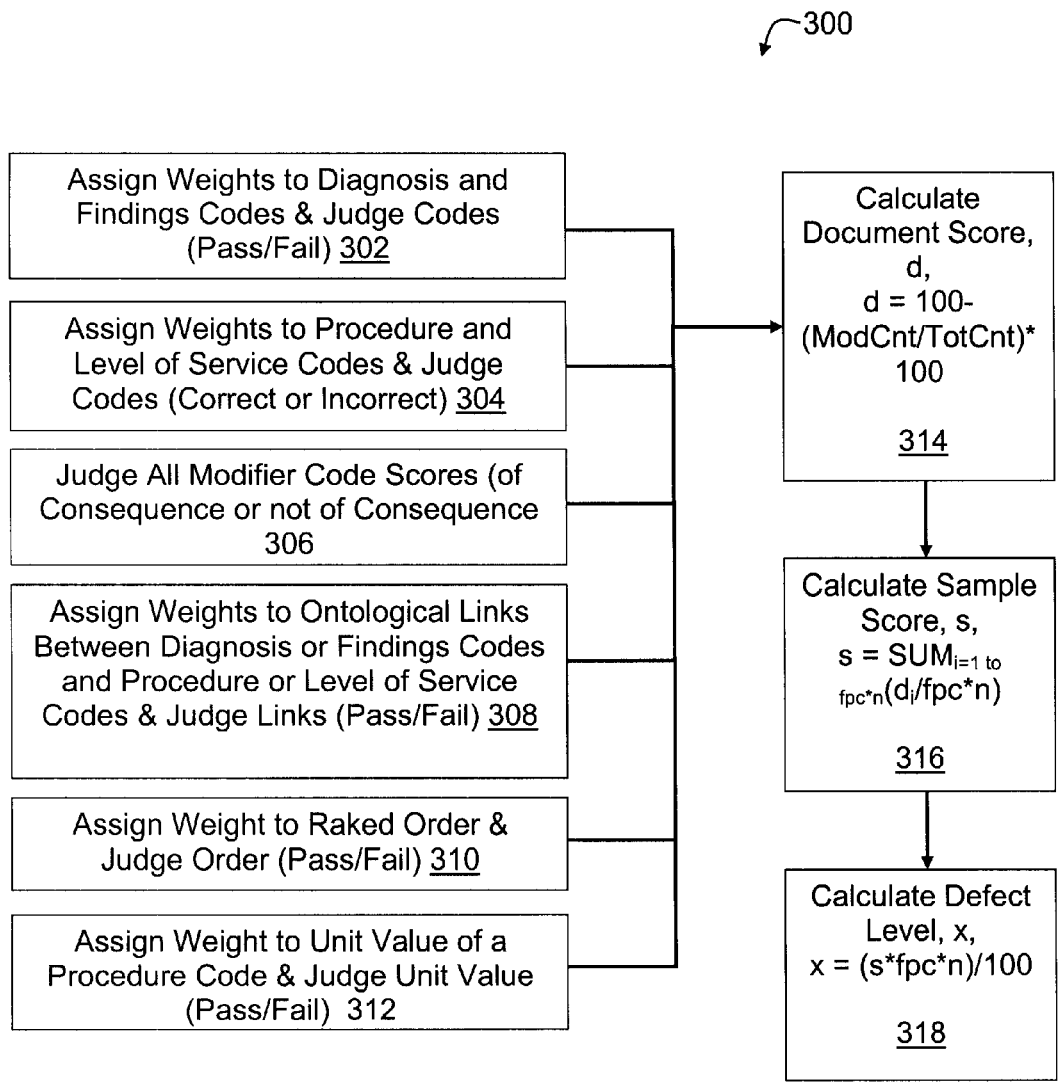
FIG. 3 is a process flow diagram of a process for calculating document score, sample score, and defect level.

FIG. 3 describes a scoring process 300 for auditing individual coded documents. Various codes, scores, links, order, and value are assigned weights and judged for use in calculating document and sample scores. For example, diagnosis and findings codes are assigned a weight of "1" and are judged as correct or incorrect (pass or fail) at 302. If judged as incorrect, the diagnosis and findings codes are further judged as of consequence. Procedure and level of service codes are assigned a weight of "2" and are judged as correct or incorrect (pass/fail) at 304. Modifier codes associated with a procedure or level of service code are assigned a weight of "1" and are judged as correct or incorrect (pass/fail) at 306. Modifier codes are optional, and thus in absence of modifier codes, no modifier code score for procedure or level of service code are provided. If modifier code scores are judged to be incorrect, the scores are further judged as either of consequence or not of consequence. All modifier code scores are judged to be of consequence, but in some instances, only some may be judged to be of consequence. Further, other weights, including but not limited to weights correlating to the Relative Value Units (RVUs) of the code, the risk associated with the coded finding, diagnosis or procedure, the frequency of usage of each code, etc., can be applied to the codes as necessary.

The relational (or ontological) links between diagnosis or findings codes and procedure or level of service codes indicate a particular diagnosis or findings code as the support for particular procedure or level of service code. These relational links are assigned a weight of 1 and are judged as correct or incorrect (pass/fail) at 308. All procedure and level of service codes are linked to at least one diagnosis or findings code. If judged to be incorrect, the links are also judged to be of consequence or not of consequence. One or more of the links can be judged to be of consequence. The ranked order in which procedure and level of service codes appear relative to other procedure codes and/or the level of service code is assigned a weight of 1 and is judged as correct or incorrect (pass/fail) at 310. If judged incorrect, the ranked order is further judged to be either of consequence or not of consequence. The ranked order of the procedure and level of service codes is always judged to be of consequence. In some implementations, the ranked order of the procedure and level of service code are not always judged to be of consequence. The unit value of a procedure code is assigned a weight of 1 and is judged correct or incorrect (pass/fail) at 312. If judged to be incorrect, the unit value is further judged to be of consequence or not of consequence. The unit value of a procedure code is always judged to be of consequence. In some implementations, the unit value of a procedure code is not always judged to be of consequence.

In some implementations, the codes, scores, links, order, and values can be assigned different weights and judgments depending on the audit process and algorithm. For example, the codes, scores, links, order and values may not always be judged of consequence.

Using the weights and judgments assigned to the codes, scores, links, order and value, a document score, d, is calculated using Equation (2) at 314.

$$d = 100 - (ModCnt/TotCnt) * 100 \quad (2)$$

where:

$$ModCnt = $$

$$SUM_{i=1 \text{ to max}(yc,yo)}(ECPTpos_i + ECPTcode_i + ECPTu_i + ECPTm_i + ECPTl_i) + SUM_{j=1 \text{ to max}(zc,zo)}(ElCDcode_j * ICDc_j)$$

$$TotCnt = SUM_{i=1 \text{ to max}(yc,yo)}(wCPTpos_i + wCPTcode_i + (wCPTu_i * CPTu_i) + (wCPTm_i * CPTm_i) + (wCPTl_i * \max(CPTlc_i, CPTlo_i)) + SUM_{j=1 \text{ to max}(zc,zo)}(wICDcode_j * ICDc_j)$$

yc is the number of post-audit procedure and/or level of service codes in the document.

zc is the number of post-audit diagnosis and/or findings codes in the document.

yo is the number of pre-audit procedure and/or level of service codes in the document.

zo is the number of pre-audit diagnosis and/or findings codes in the document.

CPTu=1 if procedure code has units, else 0.

CPTm=1 if procedure code has modifier, else 0.

CPTlc=the audited number of links for the procedure code.

CPTlo=the original number of links for the procedure code.

ECPTl is the difference between the max(CPTlc, CPTlo) and the number of links that are identical (i.e. link to the same ICD-9 code) both pre- and post-audit.

ECPTpos=wCPTpos if current rank order position of procedure code< >original position, else 0.

ECPTcode=wCPTcode if current code< >original code, else 0.

ECPTu=wCPTu if current unit< >original unit, else 0.

ECPTm=wCPTm if current modifier< >original modifier, else 0.

ElCDcode=wlCDcode if current code< >original code, else 0.

wCPTpos=1 (weight for a procedure rank order).

wCPTcode=2 (weight for a procedure or level of service code).

wCPTu=1 (weight for a procedure unit).

wCPTm=1 (weight for a procedure modifier).

wCPTl=1 (weight for a procedure link).

wlCDcode=1 (weight for a diagnosis or findings code).

ICDc=1 if the diagnosis or findings code is of consequence, else 0.

Using the weights and judgments assigned to the codes, scores, links, order, value, and the calculated document score, a sample score, s, is calculated using Equation (3) at 316.

$$S = SUM_{i=1 \text{ to } fpc*n}(d_i/fpc*n) \quad (3)$$

Using the weights and judgments assigned to the codes, scores, links, order, value, and the calculated sample score, a defect level, x, is calculated using Equation (4) at 318.

$$x = (s * fpc * n)/100 \quad (4)$$

Sample Score Interpretation

Figure 4:
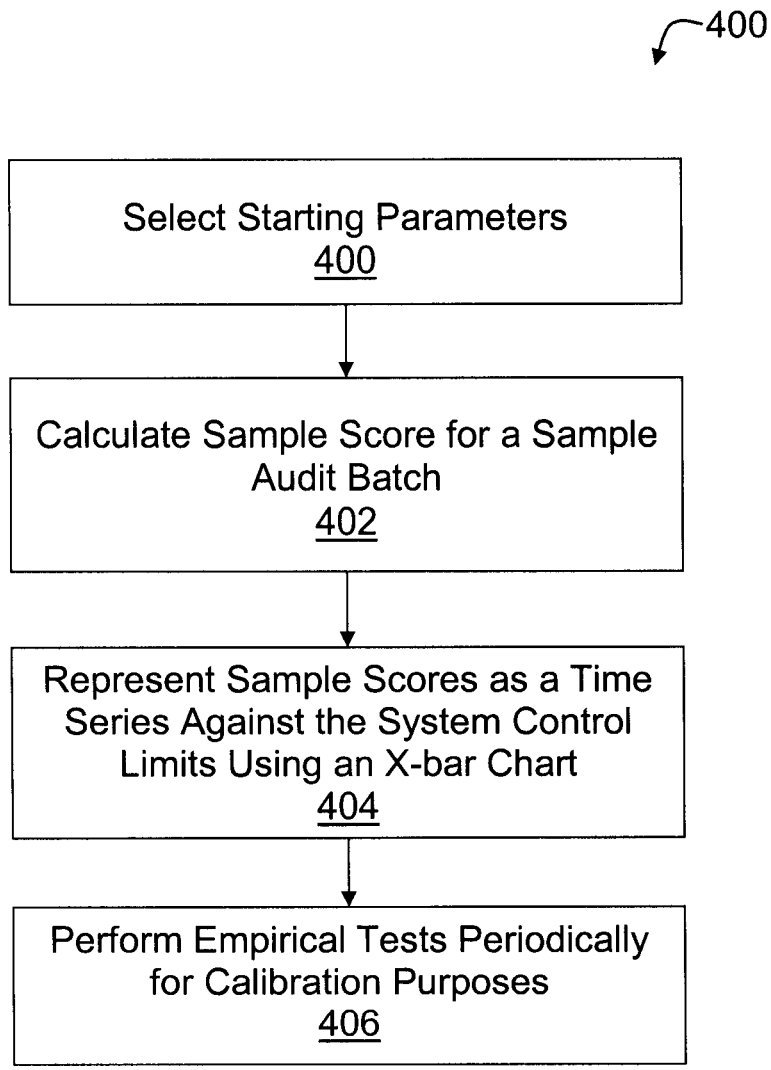
FIG. 4 is a process flow diagram of the steps for interpreting a sample score.

FIG. 4 describes a process 400 of interpreting the calculated sample score. Starting parameters are selected at 400. For example, P=0.1, H=0.04 and CV=0.03 (where P, H and CV are probabilities, not percentages) are recommended starting parameters. Using the selected starting parameters, sample scores are calculated for a sample audit batch as described in FIGS. 2-3 above at 402. A sample batch scoring system (e.g., the coder audit system 100) is designed to generate sample scores that have a linear correlation to the qualitative judgment of human auditors who may judge a coding process, as defined by the sample selection parameters, to be acceptable, marginally acceptable, or unacceptable. As such, the results of an audit can be graphically represented as a time series against the system control limits. For example, an X-bar chart (or any other suitable numerical or graphical comparison method) can be used to display the sample scores on the display 122 via a GUI (as illustrated with respect to FIGS. 5A, 5B, 5C, 5D, 5E, 5F, 5G, 5H, 5I, 5J and 5K) at 404. Because standards of acceptability may vary with time and between organizations, empirical tests are performed periodically for calibration purposes at 406. A coding process may be associated with sample scores that are consistently in control (acceptable), occasionally out of control (marginally acceptable based on an empirically derived definition of "occasionally"), or consistently out of control (unacceptable based on an empirically derived definition of "consistently"). Monthly audits are recommended with more than two sample scores determined to be out of control in a single year being considered unacceptable and requiring intervention to bring the system back in control.

In some implementations, various starting parameters and starting parameter values can be selected. In addition, periods for empirical tests can also be varied. Further, the definition of acceptable, unacceptable and marginally acceptable can vary based on factors such as the periods of testing and the number of scores out of control in such periods.

Auditor Benchmarking

The expected or observed judgment subjectivity/error proportion of the auditor, CV, can be established by making an educated estimate of the auditor's accuracy. If testing is employed to arrive at an empirically established value, then CV can be calculated as the true coefficient of variation according to Equation (5).

$$e^{sdt}-1 \qquad (5)$$

e=the mathematical constant e (also known as Euler's number).

sdt=the standard deviation of the per document audit scores (as probabilities, not percentages) so that in this implementation, CV is a real number between 0 and 1, but in other implementations, CV may be normalized to a percentage by multiplying the above formula by 100.

In some implementations, auditors can optionally be tested periodically to provide a benchmark CV value. The benchmark CV value provides a calibration of the audit results to enable comparisons across a time period and/or between different auditors. A standardized benchmark test is created to track the value of each auditor across a period of time. The benchmark test consists of a set of coded documents for the auditor to audit. The benchmark test conforms to the following three principles.

1. From one test (audit) session to the next, a significant portion of the test (e.g., at least 50%) consists of the same documents with the same codes as were present on the previous test. The remaining documents are new. The order of the documents from test to test are randomized.
2. Over time, the sample batch of documents are selected so as to reflect the distribution of encounter and document types that coders would be expected to work with under actual production conditions.
3. Test sessions are separated by sufficient time and test size is sufficiently large in order that auditors would not reasonably be expected to remember a significant percentage of their edits or corrections from one test session to the next.

Auditor scores on the benchmark tests consist of two parts. First, the coefficient of variation as calculated on the recurring documents from one test session to the next. Second, the relative variances between auditors who take the same test are calculated and may be used as a crosscheck on the intra-auditor CV variance.

Graphical User Interface (GUI)

FIGS. 5A-K are screen shots illustrating different aspects of a GUI. The various aspects and functions of the GUI includes initiating an audit (e.g., by selecting audit parameters); controlling the audit process (e.g., by modifying the defect level); displaying all information that the auditor requires to review the coded documents and make corrections to the coded documents; receiving corrections from the auditors; recording the received correction; and calculating document scores and sample scores. In addition, the GUI can be implemented to graphically display the results of the audit using charts, reports, graphs, etc.

Figure 5A:
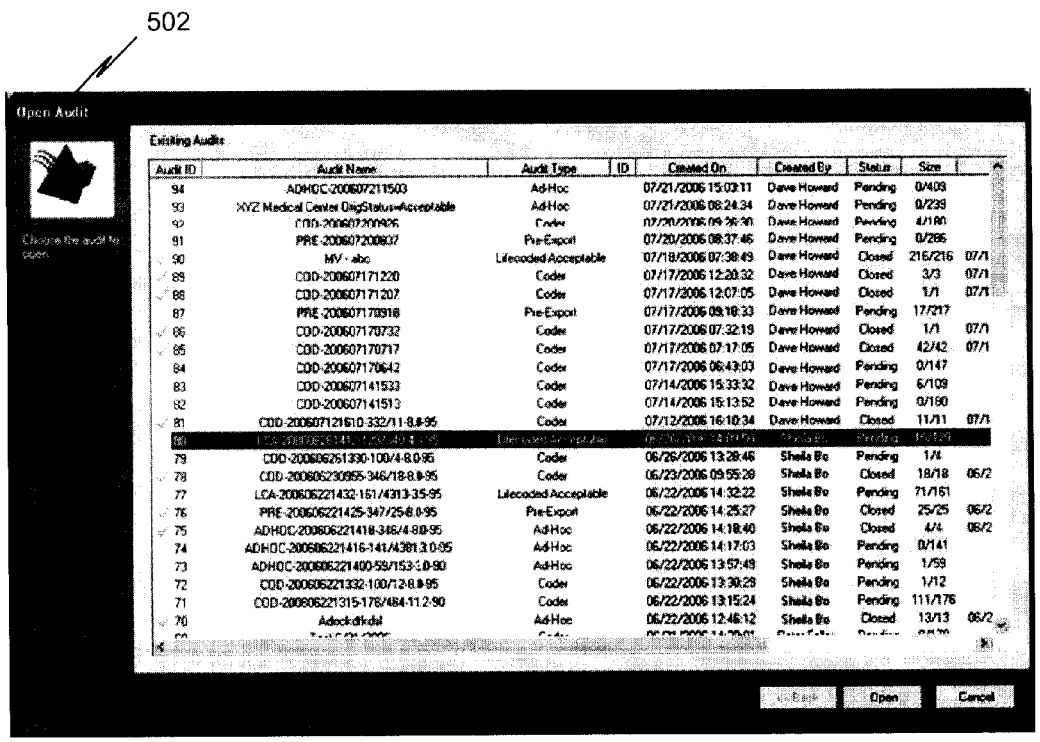
Figure 5B:
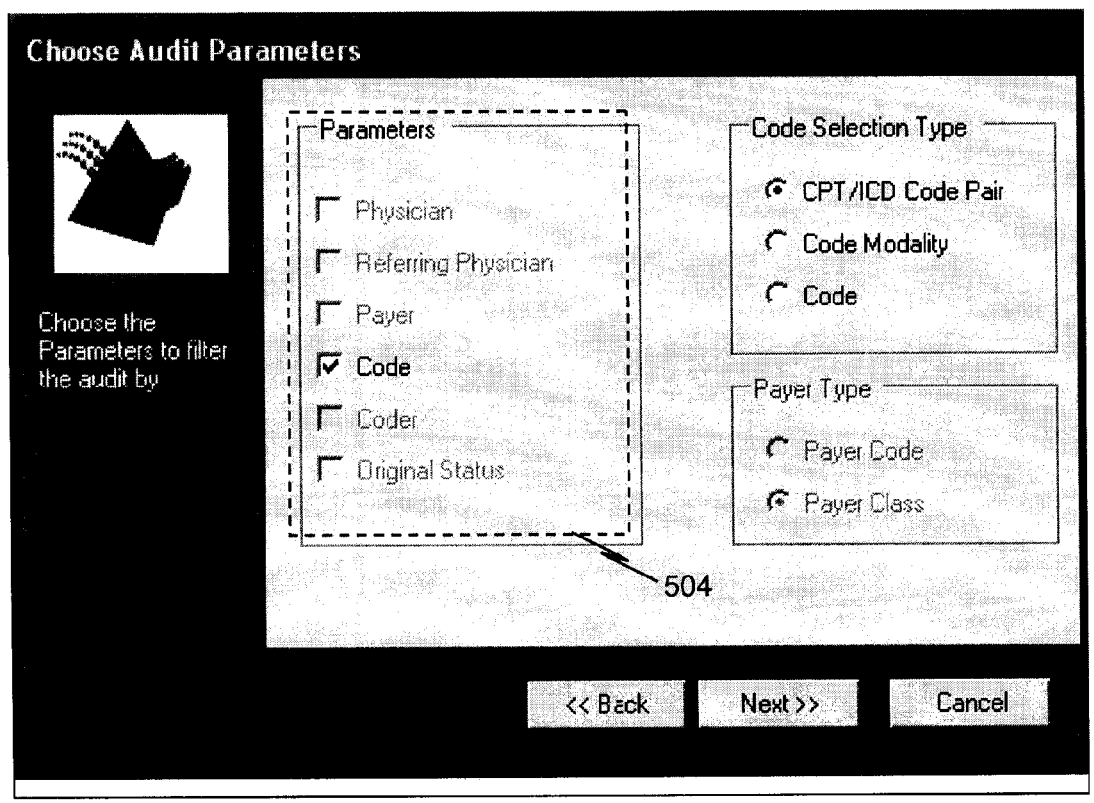

FIG. 5A shows a GUI screen 502 for allowing a user (e.g., an auditor) to open an existing audit. The user can alternatively initiate a new audit as shown in FIG. 5B. For example, a list of user selectable parameters 504 are provided. Individual screens (not shown) can be presented to fully display all selectable parameters.

Figure 5C:
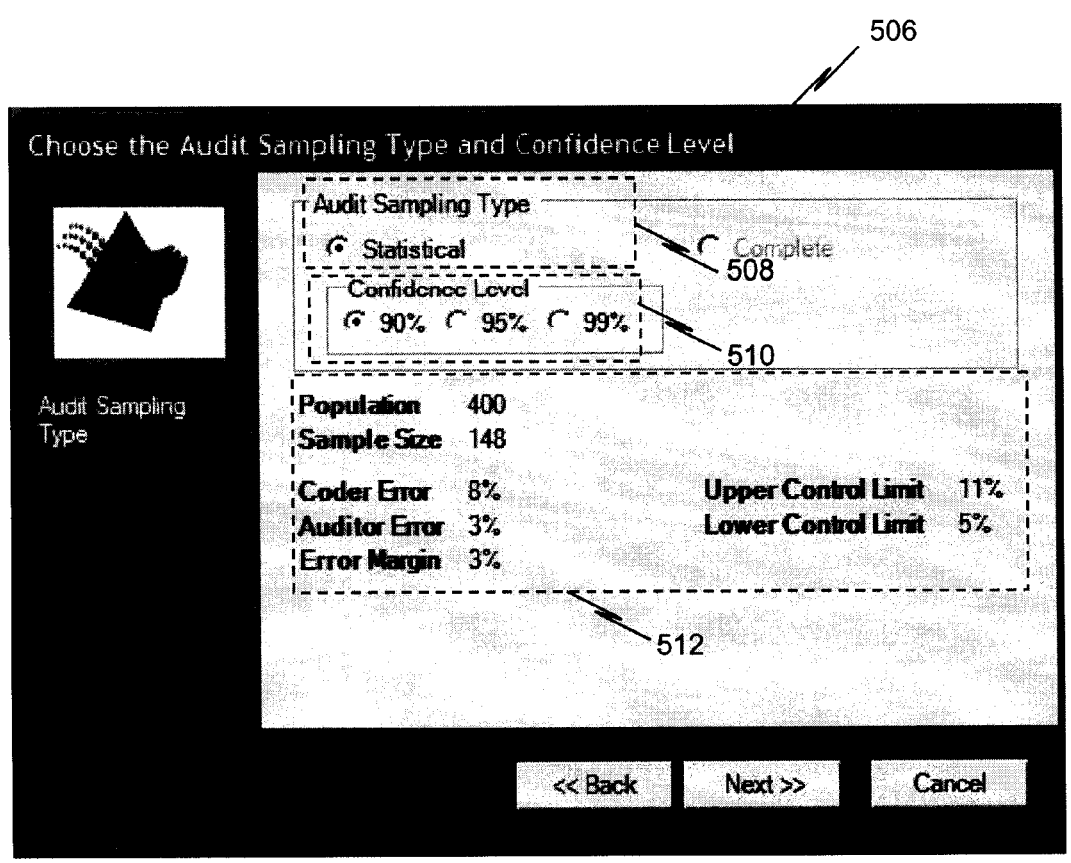

FIG. 5C shows another aspect/function of the GUI. Using an interactive screen 506 as shown in FIG. 5C, a user can select the audit sampling type 508 and confidence level 510 to have the system automatically calculate sample and other statistical parameters 512.

Figure 5D:
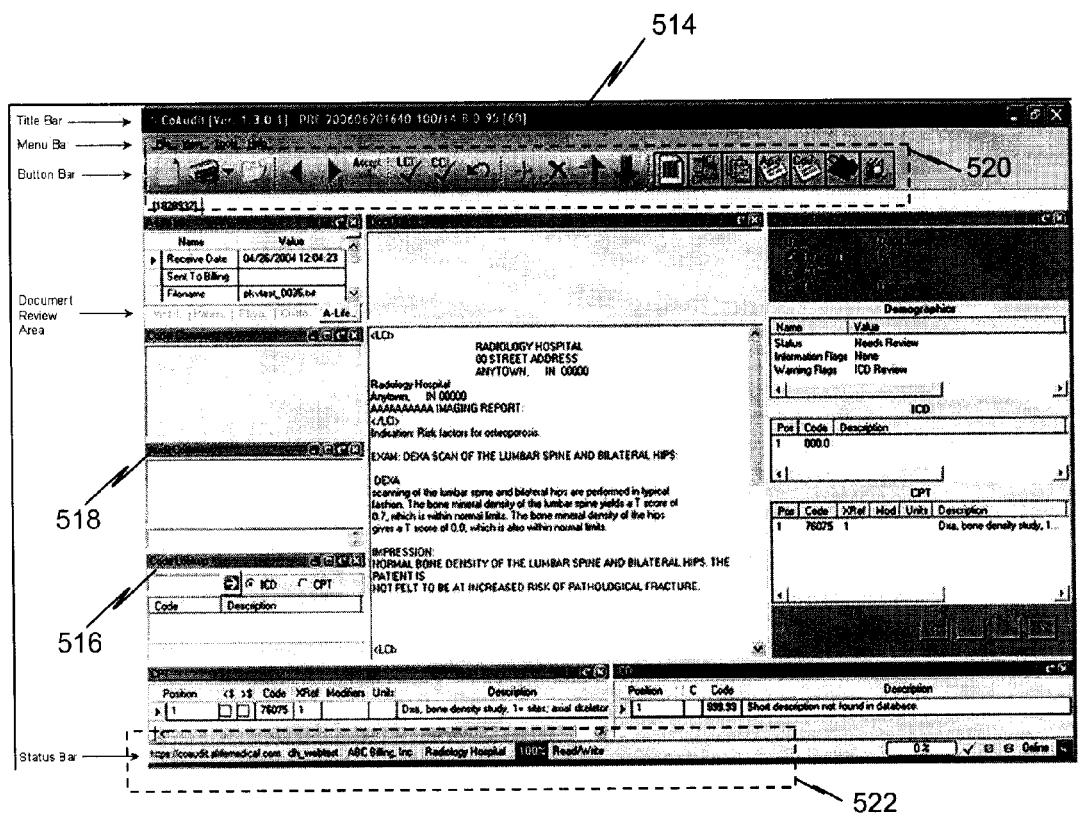

FIG. 5D shows an audit screen 514 for allowing an auditor to review the corrections made by the auditor. For example, from the audit screen 514, the auditor can review the transcription and the final ICD and CPT codes that were applied to the coded document. All visit and demographic information, the coders comments, DocIDGroup information, and Lifecode information are available. Also available is a code lookup tool 516 and a place for auditor comments 518. Buttons 520 at the top of the screen 514 can be used to hide panes that the auditor does not need to use and all panes can be resized. If the codes are incorrect, the auditor can make updates to the CPT and ICD codes, linkage, positions, modifiers and units. There is a score for the current document shown in the middle of the status bar 522 at the bottom of the window. The score starts from 100% and as changes or corrections are made by an auditor, the score lowers. Any changes made are highlighted (e.g., in red.)

Figure 5E:
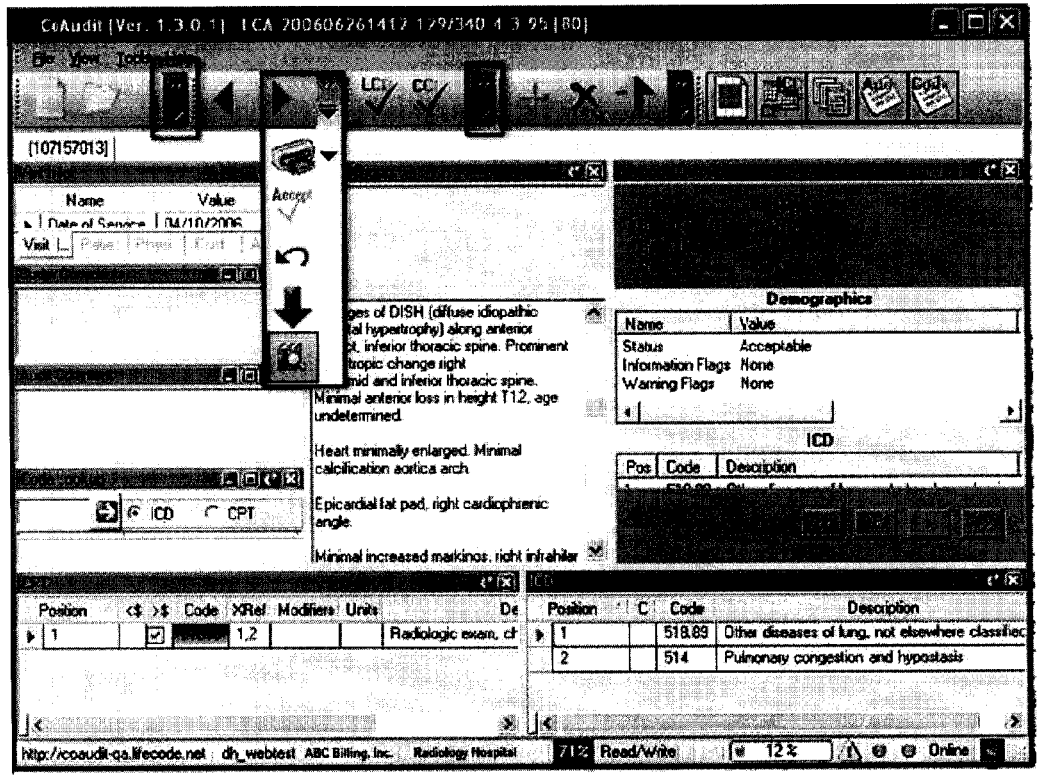
Figure 5F:
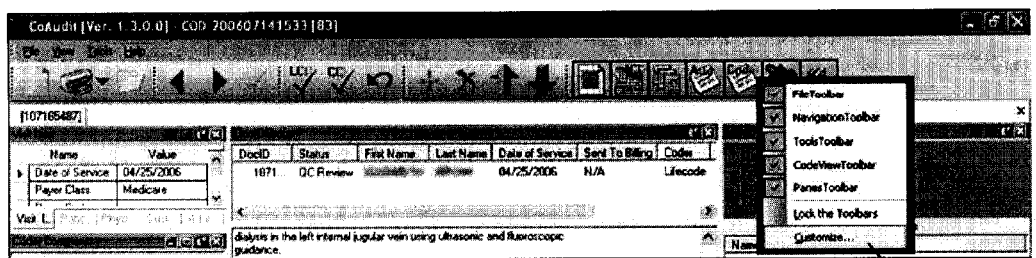

FIG. 5E illustrates that the GUI can allow users to adjust the screen resolution, resize the audit window, or customize a variety of other look-and-feel options using a drop-down menu, for example. Also, through a "Customize" dialog 524, a user can choose a custom view of the Toolbars, Commands, Menu and Toolbar Options, Keyboard Shortcuts, etc. as shown in FIG. 5F.

Figure 5G:
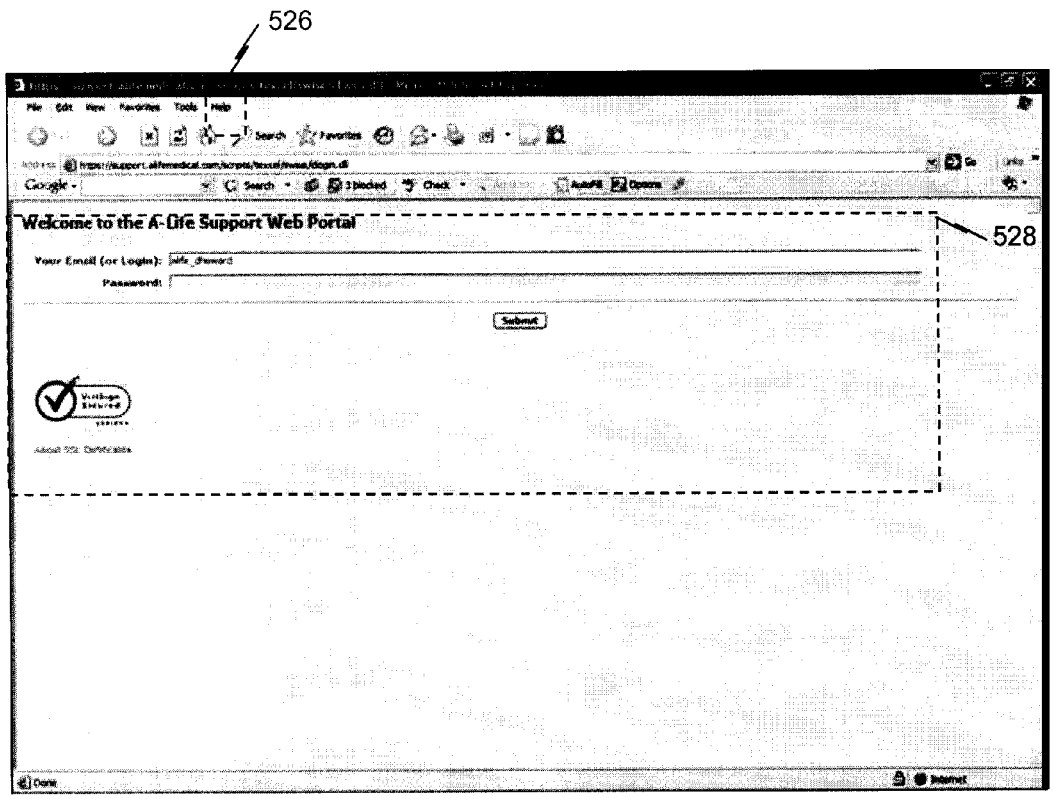

FIG. 5G shows a functionality of the GUI to allow users to report issues with the audit system. For example, when an issue arises with the audit application, the issue can be reported online by selecting Support under the Help menu 526. This launches a Support Web Portal 528 in a web browser window where the user can login and create a new ticket for the issue.

Figure 5H:
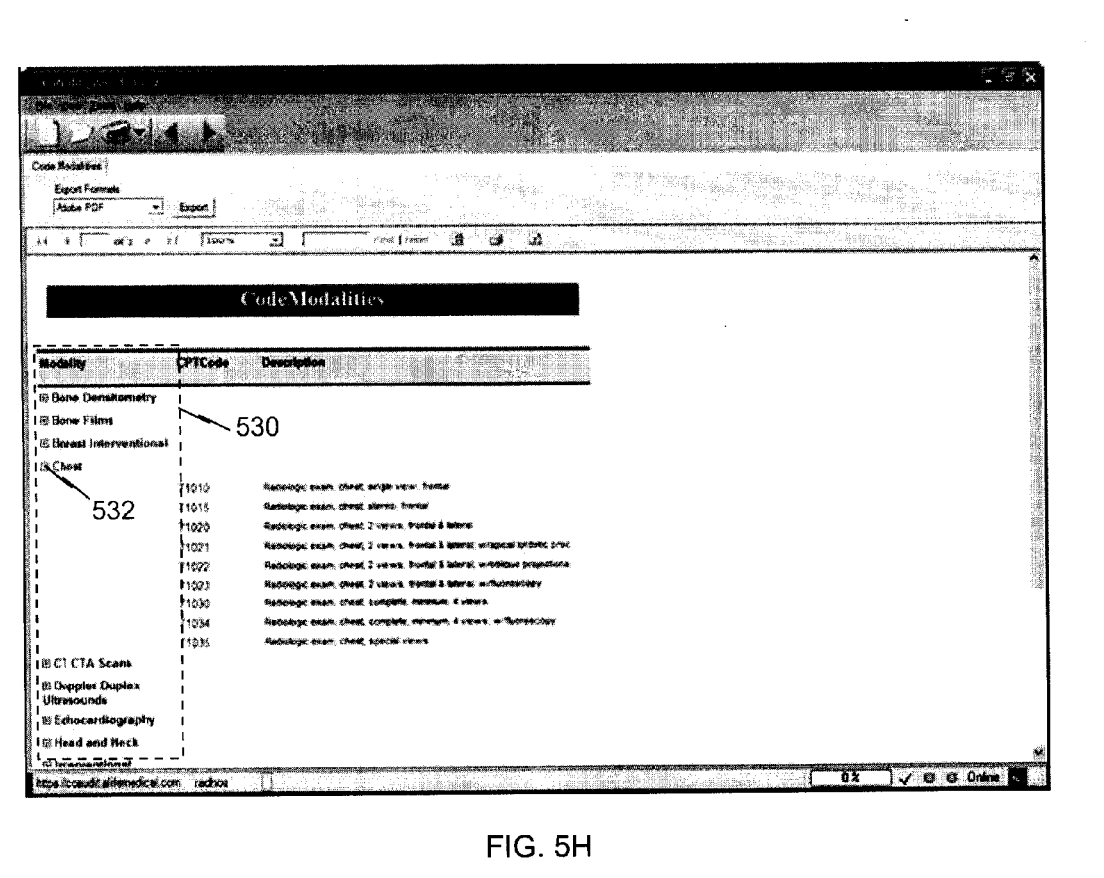

FIG. 5H shows a functionality of the GUI to organize audit reports into various subdivisions according to a variety of criteria. In the example shown in FIG. 5H, the Code Modalities Report lists the CPT codes under each modality 530 (i.e. type of equipment used to perform the procedure). To see the codes under each modality, a user can click on the plus sign 532 next to the modality name.

Figure 5I:
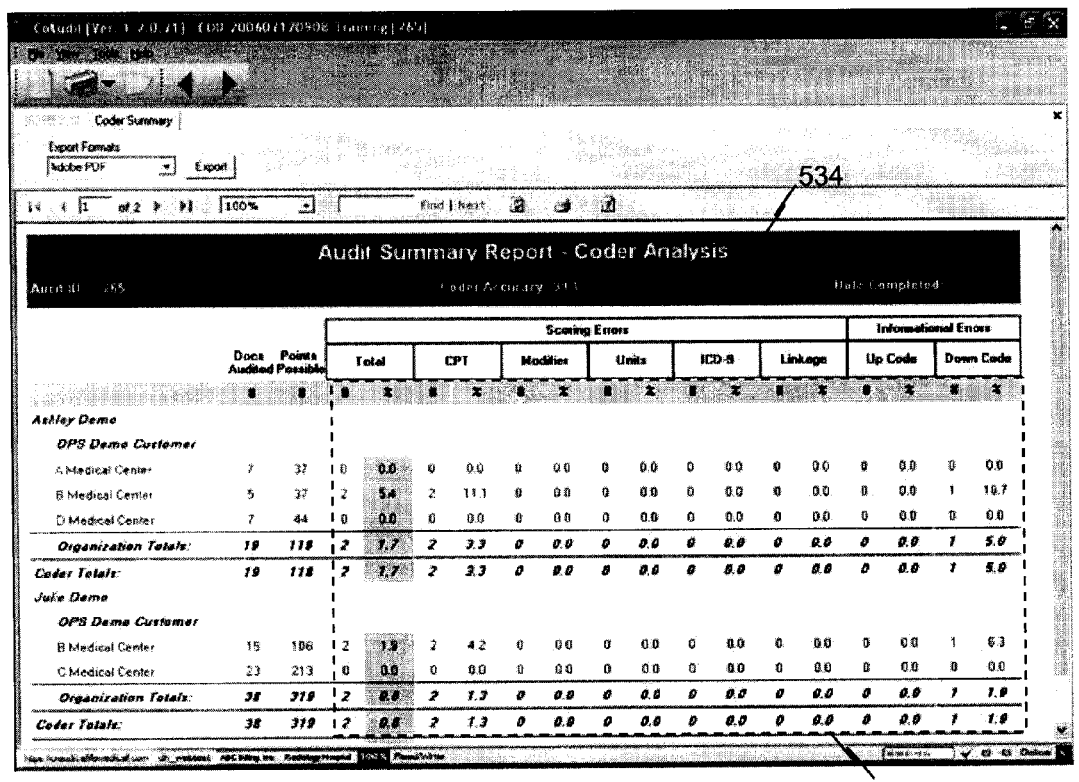

FIG. 5I shows the Code Analysis window 534 of the GUI designed to display a dashboard analysis of the audit. Scoring Errors are displayed by number of errors 536 as well as percentages of errors 538.

Figure 5J:
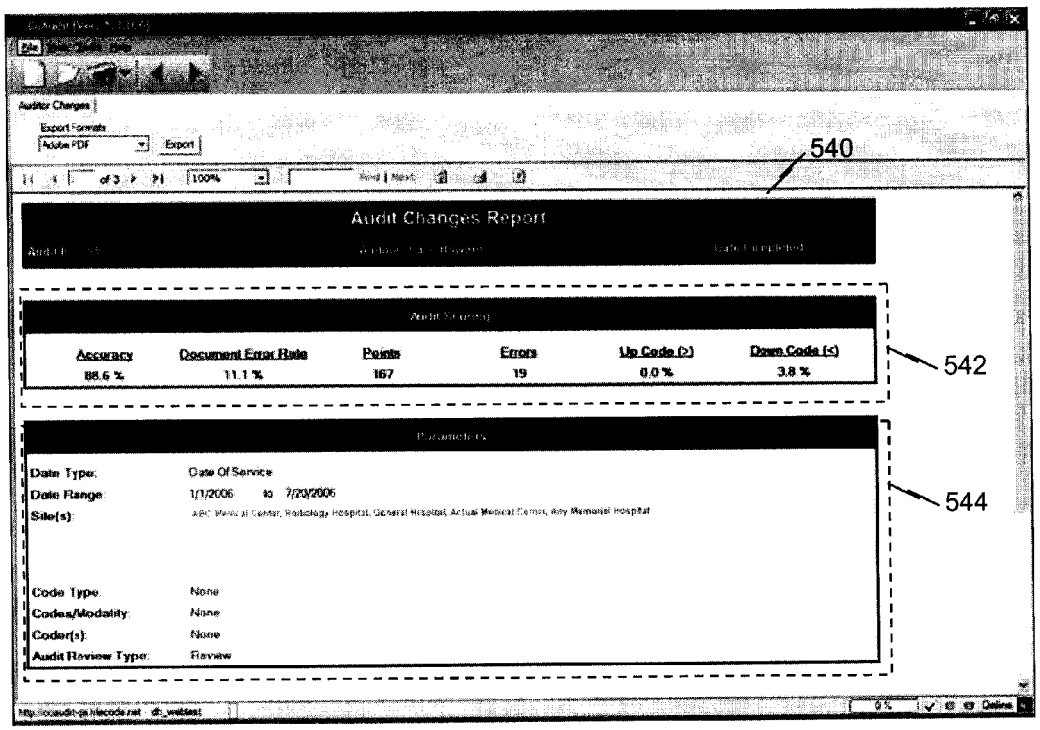

FIG. 5J illustrates a GUI window 540 for displaying the Audit Scoring 542 and Parameters 544. A scoring summary for the audit, including accuracy, document error rate, points, errors, upcode and downcode percentages are displayed. The window also lists the parameters used to create the audit.

Figure 5K:
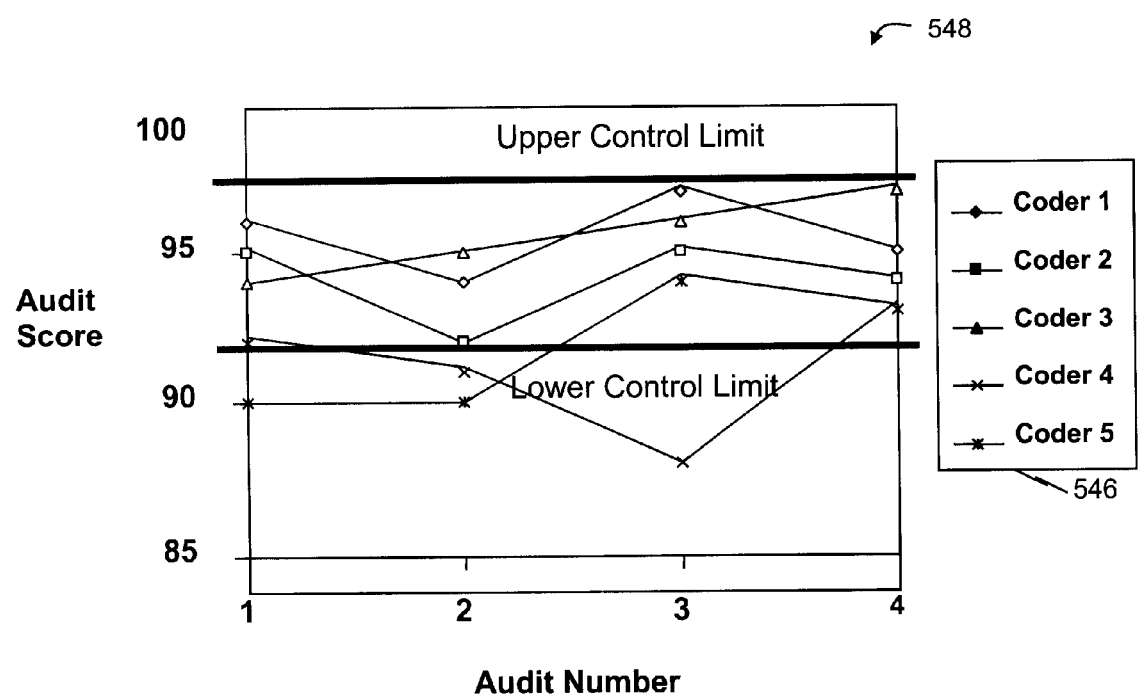

FIG. 5K shows an example graphical display of results of multiple audits. Various sample scores 546 over a period of time can be displayed and compared against upper and lower control limits. In addition, the sample scores can be compared over the period of time tested. Further, sample scores among different auditors can be compared. These results can be visually tracked using graphical display options such as an X-Bar chart 548 as illustrated in FIG. 5K.

For initiating new audits, a GUI wizard (where a "wizard" is a series of interactive screens that collect information from the user and then use that information to perform some task) that collects from the user the audit parameters needed to select the document universe, calculate the sample size and retrieve the sample batch of documents or charts for use in the audit. The setup wizard can collect the following information:

1. Audit Type: Parameters relative to how the coded document was originally created.
2. Audit Date Range: Selection of various types of date ranges, e.g. date of service, date of coding, etc.
3. Audit Sites: Selection of various parameters identifying where the medical services were performed and/or where the coding and billing for services was performed.
4. Review Type: Auditors manually select the documents to be audited or select to use a statistical determination of the audit per the Sample Selection criteria above.
5. Other Audit Parameters: The universe of documents may be optionally narrowed by the following criteria:
   a. Attending Physician(s)
   b. Referring Physician(s)
   c. Specific Codes
   d. Code Modality
   e. Payer ID Code
   f. Payer Class
   g. Coder
   h. Coding Status In some implementations, different audit parameters may be used as appropriate for a particular application.

Once the universe is specified and the sample batch of documents is selected, the GUI is used to present the sample documents/charts to the auditor and to collect the audit changes. The GUI's audit window is divided into panels and dialog boxes each of which can be displayed, hidden or repositioned and resized relative to each of the other panels that make up the GUI. Also, font and icon size, color and style can be controlled by the user. The panels, dialogs and their functions include the following:

1. Demographic Information: Identifies the patient.
2. Visit Information: Identifies the visit.
3. Physician Information: Identifies the attending physician(s) and optionally the referring physician(s).
4. Custom Fields: Any client specific information.
5. Document View: Displays the clinical source document to which the coding applies.
6. Automated Coding Information: Identifies when and where the audit document was processed by an automated coding system, if applicable.
7. Coder Comments: Any comments on the audit document that were made by the original coder.
8. Audit Comments: Any comments on the audit document made by the auditor. Audit comments can be required for any upcoding or downcoding (i.e. changes in the severity level or reimbursement level or a diagnosis or procedure).
9. Code Lookup: A diagnosis and procedure code search engine.
10. DocID Group: Links to any other documents that are associated with the current audit document. Other documents in the group can be selected for viewing in a split screen or viewing by toggling between them and the audit document, and voided documents in the group will be indicated.
11. Automated Coding Output: Document status and codes as provided by an automated coding system, if any.
12. Procedure Codes: The final procedure codes associated with the audit document following automated coding (if any) and/or human coding/review (if any). Procedure codes are CPT codes. The auditor can change, add, remove or reorder procedure codes.
13. Diagnosis Codes: The final diagnosis codes associated with the audit document following automated coding (if any) and/or human coding/review (if any). Diagnosis codes are ICD-9-CM codes. The auditor can change, add, remove, reorder or reassociate diagnosis and procedure codes.
14. LCD/NCD/CCI Dialogs: If the auditor makes any modifications to diagnosis or procedure coding, the audit tool will validate the new coding against any applicable Local Coverage Determinations (LCD), National Coverage Determinations (NCD) and Correct Coding Initiative (CCI) rules and will inform the auditor of any problems. If an auditor change creates a violation of these rules, the audit tool will present the auditor with the option of undoing or otherwise correcting the change.
15. At the completion of an audit, the auditor will be given the option of creating and exporting reports including, but not limited to: code modalities reports (reports on audit of procedures grouped by modality); automated coding system analysis; human coder analysis; auditor changes report; transcription report (details of all documents covered in the audit); X-Bar Chart analysis comparing various audited coders across time, etc.

Functionality of each panel may be further subdivided or combined with the function of other panels to the end that there are a lesser or greater number of panels without violating the spirit or intent of the invention. Other functions and panels than those discussed here may be used as required by the particular application or as determined by aesthetics or function.

Computer Implementations

In some implementations, the techniques for implementing Quality Assurance of the process of coding medical documents as described in FIGS. 1-4 can be implemented using one or more computer programs comprising computer executable code stored on a computer readable medium and executing on the coder audit system 100. The computer readable medium may include a hard disk drive, a flash memory device, a random access memory device such as DRAM and SDRAM, removable storage medium such as CD-ROM and DVD-ROM, a tape, a floppy disk, a CompactFlash memory card, a secure digital (SD) memory card, or some other storage device.

In some implementations, the computer executable code may include multiple portions or modules, with each portion designed to perform a specific function described in connection with FIGS. 1-4 above. In some implementations, the techniques may be implemented using hardware such as a microprocessor, a microcontroller, an embedded microcontroller with internal memory, or an erasable programmable read only memory (EPROM) encoding computer executable instructions for performing the techniques described in connection with FIGS. 1-4. In other implementations, the techniques may be implemented using a combination of software and hardware.

Processors suitable for the execution of a computer program include, by way of example, both general and special purpose microprocessors, and any one or more processors of any kind of digital computer, including graphics processors, such as a GPU. Generally, the processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

A number of embodiments have been described. Nevertheless, it will be understood that various modifications may be made without departing from the scope of the claims. For example, in some implementations, the coder audit system 100 is implemented entirely as a single application (e.g., a smart client application 108), which can perform operations including processes 200, 300 and 400 as described with respect to FIGS. 2, 3 and 4. Accordingly, other embodiments are within the scope of the following claims.

What is claimed is:

1. A method performed by a computer of evaluating coded medical documents, the method comprising:
   receiving, by a computer, audit parameters comprising an expected coder error level, and receiving an empirically established expected auditor error level of an auditor based on an assessment of the auditor;
   selecting, by the computer, a sample batch of coded medical documents for auditing by the auditor, the sample batch of coded medical documents selected from a universe of coded medical documents stored on one or more storage devices, the selection based at least in part on the received audit parameters;
   receiving, by the computer, audited medical documents corresponding to the selected sample batch of coded medical documents, wherein the audited medical documents include corrections by the auditor;
   calculating, by the computer, a medical document score for each of the audited medical documents based on medical document corrections received from the auditor and applying weighted factors, wherein the weighted factors comprise predefined weights assigned to diagnosis and procedure codes in each of the audited medical documents;
   calculating, by the computer, a sample score for the audited medical documents based on a function of the calculated medical document scores;
   designating, by the computer, at least one of an upper control limit and a lower control limit based on the expected auditor error level; and
   comparing, by the computer, the sample score against the at least one of the upper and lower control limits to determine an acceptability of the sample score.

2. The method of claim 1, further comprising calculating a defect level based on the sample score.

3. The method of claim 2, further comprising adjusting the defect level to account for the expected auditor error level of the auditor.

4. The method of claim 1, further comprising:
   repeating the evaluation over a period of time to compile a plurality of sample scores; and
   tracking a measure of variance in the compiled sample scores across the period of time.

5. A method of claim 4, further comprising tracking a measure of variance between the auditor and other auditors.

6. The method of claim 1, wherein the medical document corrections and a type of each of the corrections are recorded for the sample batch of coded medical documents.

7. The method of claim 1, further comprising recording the medical document corrections.

8. The method of claim 1, wherein calculating the sample score for the audited medical documents based on a function of the calculated medical document scores comprises obtaining a summation of the calculated medical document scores.

9. The method of claim 1, further comprising designating a quality of the coding process, accounting for the error level of the auditor, as being one of an acceptable quality, a marginal quality, and an unacceptable quality.

10. The method of claim 1, wherein calculating the medical document score comprises obtaining a summation of the weighted factors.

11. A system of evaluating coded medical documents, the system comprising:
    a user interface device; and
    one or more computers communicatively coupled to the user interface device, the one or more computers including a processor and a display configured to provide a graphical user interface to an auditor, the one or more computers configured to perform operations including:
    receive audit parameters comprising an expected coder error level, and receiving an empirically established expected auditor error level of an auditor based on an assessment of the auditor;
    select a sample batch of coded medical documents for auditing by the auditor, the sample batch of coded medical documents selected from a universe of coded medical documents stored on one or more storage devices, the selection based at least in part on the received audit parameters;

receive audited medical documents corresponding to the selected sample batch of coded medical documents, wherein the audited medical documents include corrections by the auditor;

calculate a medical document score for each of the audited medical documents based on medical document corrections received from the auditor and applying weighted factors, wherein the weighted factors comprise predefined weights assigned to diagnosis and procedure codes in each of the audited medical documents;

calculate a sample score for the audited medical documents based on a function of the calculated medical document scores;

designate at least one of an upper control limit and a lower control limit based on the expected auditor error level; and compare the sample score against the at least one of the upper and lower control limits to determine an acceptability of the sample score.

12. The system of claim 11, wherein the one or more computers are further configured to calculate a defect level based on the sample score.

13. The system of claim 12, wherein the one or more computers are further configured to facilitate adjustment of the defect level to account for the expected auditor error level of the auditor.

14. The system of claim 11, wherein the one or more computers are further configured to:
allow a repeat of the evaluation over a period of time to compile a plurality of sample scores; and
track a measure of variance in the complied sample scores across the period of time.

15. A system of claim 14, wherein the one or more computers are further configured to track a measure of intra-auditor variation.

16. The system of claim 11, wherein the medical document corrections and a type of each of the corrections are recorded for the sample batch of coded medical documents.

17. The system of claim 11, wherein the graphical user interface is configured to facilitate recording of the medical document corrections.

18. The system of claim 11, wherein the one or more computers is further configured to facilitate the calculation of the sample score for the audited medical documents based on a function of the medical document scores comprising a summation of the calculated medical document scores.

19. The system of claim 11, wherein the one or more computers are further configured to define a quality of the coding process, accounting for the error level of the auditor, as being one of an acceptable quality, a marginal quality, and an unacceptable quality.

20. The system of claim 11, wherein each medical document score comprises a summation of the weighted factors.

21. A non-transitory computer readable medium storing instructions that when executed by a computer cause the computer to perform operations comprising:
receiving an empirically established expected auditor error level of an auditor based on an assessment of the auditor;
selecting audit parameters comprising an expected coder error level and the empirically established expected auditor error level of the auditor;
selecting a sample batch of coded medical documents for auditing by the auditor, the sample batch of coded medical documents selected from a universe of coded medical documents stored on one or more storage devices, the selection based at least in part on the selected audit parameters;

receiving audited medical documents corresponding to the selected sample batch of coded medical documents, wherein the audited medical documents include corrections by the auditor;

calculating a medical document score for each of the audited medical documents based on medical document corrections received from the auditor and applying weighted factors, wherein the weighted factors comprise predefined weights assigned to diagnosis and procedure codes in each of the audited medical documents;

calculating a sample score for the audited medical documents based on a function of the calculated medical document scores;

designating at least one of an upper control limit and a lower control limit based on the expected auditor error level; and comparing the sample score against the at least one upper and lower control limits to determine an acceptability of the sample score.

22. The non-transitory computer readable medium of claim 21, further operable to cause the computer to calculate a defect level based on the sample score.

23. The non-transitory computer readable medium of claim 22, further operable to cause the computer to adjust the defect level to account for the expected auditor error level of the auditor.

24. The non-transitory computer readable medium of claim 21, further operable to cause the computer to perform operations comprising:
repeating the evaluation over a period of time to compile a plurality of sample scores; and
tracking a measure of variance in the sample scores across the period of time.

25. The non-transitory computer readable medium of claim 24, further operable to cause the computer to track a measure of variance between the auditor and other auditors.

26. The non-transitory computer readable medium of claim 21, further operable to cause the computer to perform operations comprising embedding the corrections within the sample batch of coded medical documents.

27. The non-transitory computer readable medium of claim 21, further operable to cause the computer to perform operations comprising facilitating recording of the received corrections.

28. The non-transitory computer readable medium of claim 21, further operable to cause the computer to facilitate calculation of the sample score for the audited medical documents based on a function comprising a summation of the calculated medical document scores.

29. The non-transitory computer readable medium of claim 21, further operable to cause the computer to define a quality of the coding process, accounting for the error level of the auditor, as being one of an acceptable quality, a marginal quality, and an unacceptable quality.

30. The non-transitory computer readable medium of claim 21, further operable to cause the computer to calculate each medical document score by summing the weighted factors.

\* \* \* \* \*